US006861001B2

(12) United States Patent
Lee et al.

(10) Patent No.: US 6,861,001 B2
(45) Date of Patent: Mar. 1, 2005

(54) METHODS FOR REMOVAL, PURIFICATION, AND CONCENTRATION OF VIRUSES, AND METHODS OF THERAPY BASED THEREUPON

(75) Inventors: William Lee, Cambridge, MA (US); Jeffrey R. Morgan, Sharon, MA (US); Martin L. Yarmush, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 346 days.

(21) Appl. No.: 09/728,882

(22) Filed: Dec. 1, 2000

(65) Prior Publication Data

US 2001/0034055 A1 Oct. 25, 2001

Related U.S. Application Data

(60) Provisional application No. 60/168,551, filed on Dec. 2, 1999.

(51) Int. Cl.[7] .............................................. B01D 61/00
(52) U.S. Cl. ...................... 210/651; 210/645; 210/650; 210/653; 210/500.36; 210/500.35
(58) Field of Search ................................ 210/650, 651, 210/653, 645, 490, 500.36, 500.35; 264/48

(56) References Cited

U.S. PATENT DOCUMENTS

| 4,808,315 | A | | 2/1989 | Manabe et al. ............. 210/645 |
| 4,857,196 | A | | 8/1989 | Manabe et al. ........... 210/500.3 |
| 4,874,522 | A | | 10/1989 | Okamoto et al. ........... 210/645 |
| 4,919,809 | A | | 4/1990 | Yamamoto et al. ..... 210/500.23 |
| 5,076,933 | A | | 12/1991 | Glenn et al. ................ 210/641 |
| 5,096,637 | A | | 3/1992 | DiLeo et al. .............. 264/45.1 |
| 5,447,859 | A | | 9/1995 | Prussak ...................... 435/239 |
| 5,667,684 | A | * | 9/1997 | Motomura et al. ......... 210/506 |
| 5,808,315 | A | * | 9/1998 | Manabe et al. |
| 5,981,038 | A | * | 11/1999 | Weimer et al. |
| 6,022,478 | A | * | 2/2000 | Baurmeister et al. |
| 6,258,870 | B1 | * | 7/2001 | Hubbel et al. |
| 6,451,352 | B1 | * | 9/2002 | Yvin et al. .................. 424/680 |

FOREIGN PATENT DOCUMENTS

| EP | 0490940 B1 | * | 6/1990 |
| WO | 90/05018 | * | 5/1990 |
| WO | WO 99/07458 | | 2/1999 |
| WO | WO 99/51316 | | 10/1999 |

OTHER PUBLICATIONS

Dytnerskii et al., "Study Of The Porous Structure and Selectivity Properties of Membranes Obtained By Plasma Polymerization In A Glow Discharge", Kolloidn.Zh., 1982, vol. 44, No. 6, pp 1024–1028.

Lee et al., "Design of urea–permeable anion–exchange membrane by radiation–induced graft polymerization", Journal of Membrane Science, vol. 81, pp. 295–305 (1993).

(List continued on next page.)

*Primary Examiner*—Ana Fortuna
(74) *Attorney, Agent, or Firm*—Fish & Richardson P.C.

(57) ABSTRACT

The invention is based on the discovery that certain membranes, which include side chains or molecular "brushes" having, for example, tertiary amino functional groups, can be used as highly effective filters to capture viruses/virus particles from liquids without removal of proteins. New methods based on this discovery include removing viruses from liquids such as blood or plasma, removing viruses from pharmaceuticals, concentrating and/or purifying viruses, e.g., for use in gene therapy, and producing recombinant viruses in new bioreactors. The invention also includes new methods of therapy or adjunct therapy for viral infections, in which a patient's blood or plasma is filtered through the membranes to remove viruses to reduce the viral load. The invention also includes new bioreactors and viral filters containing the membranes.

28 Claims, 4 Drawing Sheets

OTHER PUBLICATIONS

Lee, "Study on Charged Brushes Grafted in Polymeric Materials by Radiation–Induced Graft Polymerization and Their Applications as Functional Materials", Dept. of Chemistry and Biotechnology, Graduate School of Engineering, The University of Tokyo, pp 1–195.

Konishi et al., "Binary metal–ion sorption during permeation through chelating porous membranes", Journal of Membrane Science, vol. 111, No. 1, pp 1–6 (1996).

Tsuneda et al., "Hydrodynamic Evaluation of Three–Dimensional Adsorption of Protein to a Polymer Chain Grafted onto a Porous Substrate", Journal of Colloid and Interface Science, vol. 176, No. 1, pp 95–100 (1995).

Matoba et al., "Highly Efficient Enzyme . . . Tentacle Polymer Chains", BIO/TECHNOLOGY, vol. 13, pp 795–797 (1995).

Lee et al., "Tailoring a Brush–Type Interface Favorable for Capturing Microbial Cells", Journal of Colloid and Interface Science, vol. 200, No. 1, pp 66–73 (1998).

Lee et al., "Adsorption Kinetics of Microbial Cells . . . Radiation–Induced Graft Polymerization", Biotechnol. Prog., vol. 12, No. 2, pp 178–183 (1996).

Lee et al., "Comparison of Formation Site of Graft Chain between Nonporous and Porous Films Prepared by RIGP", Chem. Mater., vol. 8, pp 2618–2621(1996).

Saito et al., "Preparation and Evaluation of Novel . . . Graft Polymerization", Nippon Ion Kokan Gakkaishe, vol. 7, No. 2, pp 130–141 (1996).

LeDoux et al., "Kinetics of Retrovirus Production and Decay", Biotechnology and Bioengineering, vol. 63, No. 6, Jun. 20, 1999, pp 654–662 (1999).

* cited by examiner

METHODS FOR REMOVAL, PURIFICATION, AND CONCENTRATION OF VIRUSES, AND METHODS OF THERAPY BASED THEREUPON

CROSS-REFERENCE TO RELATED APPLICATION

This application claims benefit of priority of U.S. Provisional Application No. 60/168,551, filed on Dec. 2, 1999, which is incorporated herein by reference in its entirety.

STATEMENT AS TO FEDERALLY-SPONSORED RESEARCH

This research was funded in part by National Institutes of Health grant P01-28528, NSF BS9800617. Accordingly, the United States Government has certain interest and rights to this invention.

FIELD OF THE INVENTION

The invention relates to methods of using membranes for removing, capturing, and purifying viruses from liquids, for example, plasma and commercial biological products, and methods of therapy based on such methods.

BACKGROUND OF THE INVENTION

Recombinant retroviruses can be used for gene transfer and are under consideration for use in gene therapy (*Science* 260:926–932, 1993), e.g., for in vivo or ex vivo gene therapy either as vectors targeted to specific tissues or as lenti-virus vectors that transduce non-dividing cells. The relatively large size (e.g., ~100 nm) and complexity of the retroviruses, as well as their instability and sensitivity to inhibitors have presented significant challenges to the development of processes for the purification and concentration of viruses, particularly when large-scale production is desired. However, several problems limit the effectiveness of recombinant retroviruses, including relatively low titers of viruses, instability of the particles, and the lack of facile methods for the rapid concentration and purification of bioactive viral particles (*Hum. Gene Ther.,* 5:19–28, 1994; *Bioseparation,* 6:211–288, 1996; *Curr. Opin. Biotechnol.,* 9:177–185, 1998; *Biotechnol. Prog.,* 15:1–11, 1999). The development of new processes for the production of stable, concentrated recombinant retroviruses that can yield high gene transfer efficiencies is thus one of several challenges facing the field of gene therapy. Moreover, as applications of in vivo gene transfer become more numerous, methods for the large-scale purification of viruses will also be required.

Additionally, a need exists for inexpensive, rapid, and effective methods for removing viruses from pooled plasma (e.g., as identified, for example, by the Consortium for Plasma Science LLC), plasma derivatives, blood banks, living tissue, a patient's blood, or commercial biological products (e.g., complex biopharmaceutical preparations such as recombinant protein preparations).

SUMMARY OF THE INVENTION

The invention is based on the discovery that certain membranes, that include side chains or molecular "brushes" having, for example, tertiary amino functional groups, can be used as highly effective filters to capture viruses and virus particles from liquids with minimal removal of proteins. New methods based on this discovery include removing viruses from liquids such as blood or plasma, removing viruses from pharmaceuticals, concentrating and/or purifying viruses, e.g., for use in gene therapy, and producing recombinant viruses in new bioreactors. The invention also includes new methods of therapy or adjunct therapy for viral infections, in which a patient's blood or plasma is filtered through the membranes to remove viruses to reduce the viral load. The invention also includes new bioreactors to produce viruses and viral filters containing the membranes.

In one embodiment, the invention features a method for removing a virus from a liquid sample. The method includes the steps of (a) obtaining a membrane engrafted with polymeric side chains, where the membrane has a nominal pore size between about 20 nm and about 1000 nm (e.g., about 200 nm to about 500 nm, e.g., about 240 nm, about 340 nm, or about 460 nm); and (b) passing the sample through the membrane to remove viruses from the sample. The polymeric side chains can have one or more (e.g., one, two, three, or more kinds of) functional groups that interact with (e.g., can bind to or react with) viruses (or virus particles). Examples of suitable functional groups include charged functional groups such as secondary, tertiary, or quaternary amines.

The method can be effective, for example to remove at least about 99.999% (e.g., at least about 99.9999%, about 99.99999%, or about 99.999999%) of virus particles from the sample, corresponding to at least a five-log reduction in viral titer, sufficient to remove substantially all of the virus particles in a sample containing about $1\times10^5$, $1\times10^6$, $1\times10^7$, $1\times10^8$, or more of such particles.

The virus can be, for example, a retrovirus such as HIV or a hepatitis virus.

The sample can, for example, include a protein (e.g., the activity of which is to be retained). In this case, preferably less than about 10% (e.g., less about 5%, about 2%, about 1%, about 0.1%, or less) of the protein is removed from the sample in the passing step. The sample can, for example, be a plasma sample, and the method can result in less than a five-fold increase in the plasma sample's clotting time (e.g., as determined in prothrombin time (PT) and/or activated partial thromboplastin time (APTP) assays).

The sample flows through the membrane at a rate of 1 to 1000 ml/min (e.g., about 20 to about 200 ml/min) per square centimeter of membrane (i.e., corresponding to a flow rate of about 0.057 to about 57 ml/min for a 2 cm-long hollow fiber of inner diameter of 0.19 cm, and, thus, an inner circumference of 0.0284).

The method can also include the step of eluting the virus from the membrane with an eluent solution (e.g., a sodium chloride solution) to obtain a suspension of substantially purified virus in the eluent solution (e.g., in bioactive form). In some cases, the purified virus can be concentrated more than 100-fold relative to the sample.

Another embodiment of the invention features a method of removing viruses from the blood of an individual having a viral infection (e.g., a hepatitis virus or human immunodeficiency virus). The method includes the steps of (a) obtaining a membrane engrafted with polymeric side chains having tertiary amino functional groups, the membrane having a nominal pore size between 20 nm and 1000 nm (e.g., about 200 nm to about 500 nm, e.g., about 240 nm, about 340 nm, or about 460 nm); (b) sequestering blood cells from the individual's blood using a plasma separator to produce sequestered blood cells and plasma; (c) passing the plasma through the membrane to produce filtered plasma; (d) combining the filtered plasma with the sequestered blood cells to produce filtered blood; and (e) returning the filtered blood to the individual.

Still another embodiment of the invention features a device for removing viruses from a liquid sample. The device includes a membrane engrafted with polymeric side chains having one or more functional groups that interact with viruses (e.g., positively charged functional groups, amino groups), the membrane having a nominal pore size between 20 nm and 1000 nm (e.g., about 200 nm to about 500 nm, e.g., about 240 nm, about 340 nm, or about 460 nm). The device can also include tubing, connectors, housings, and other components.

Yet another embodiment of the invention features a method of generating virus particles. The method includes the steps of (a) culturing a virus infected cell line in a culture medium under conditions suitable for the production of viruses (e.g., at physiological temperature, pH); (b) flowing culture medium containing virus particles through a filter that includes a membrane engrafted with polymeric side chains having tertiary amino functional groups, the membrane having a nominal pore size between 20 nm and 1000 nm (e.g., about 200 nm to about 500 nm, e.g., about 240 nm, about 340 nm, or about 460 nm); (c) eluting virus particles from the membrane; and, optionally, (d) storing the virus particles under conditions suitable for long-term storage (e.g., at 4° C.).

Still another embodiment of the invention features a device for generating virus particles. The device includes a bioreactor comprising a vessel suitable for containing a culture medium for the generation of viruses; and a filter that includes at least one membrane (e.g., one or more hollow fibers) engrafted with polymeric side chains having tertiary amino functional groups, the membrane having a nominal pore size between 20 nm and 1000 nm (e.g., about 200 nm to about 500 nm, e.g., about 240 nm, about 340 nm, or about 460 nm). The filter is functionally connected to the bioreactor (e.g., with tubing, or connectors) so as to allow virus particles produced in the bioreactor to contact the membrane. The bioreactor can also include a heater to heat the vessel and/or a refrigerator to cool the filter.

In any of the above embodiments, the membrane can include, for example, polyethylene, and the polymeric side chains can, for example, include diethylaminated poly (glycidyl methacrylate) ("DEA-PGMA") or other PGMA derivatives, other aminated polymers, or sulfonylated polymers. The polymeric side chains can, for example, have an average length between about 50 nm and about 2000 nm (e.g., about 500 nm to about 1000 nm), corresponding to anywhere from several hundred to tens of thousands of monomer units. Anywhere from about $1.0 \times 10^{16}$ to about $1.0 \times 10^{20}$ (e.g., about $1.0 \times 10^{17}$ to about $1.0 \times 10^{18}$) of the side chains can be engrafted per square meter of the membrane's surface area. The membrane can, for example, have a degree of grafting ("DG") between about 50% and about 500% (e.g., about 150% to about 300%).

As used herein, the term "brush" refers to a functionalized polymeric "side chain" that is or can be engrafted to a membrane. The side chain can be any polymer, but is preferably an easily functionalizable polyvinyl polymer such as poly(glycidyl methacrylate) ("PGMA"), which has one reactive epoxide group per repeat. The length of the brush can vary, as can the density (i.e., the number of brushes per unit surface area of the membrane) and identity of the attached functional groups. Suitable functional groups for virus capture include amines (e.g., secondary, tertiary, or quaternary amines). Amines can be formed, for example, by treating PGMA with an alkylamine, an arylamine, or an alkylarylamine. At physiological pH, many of these amines would bear a positive charge. If a negative charge is preferred for a specific application, the brushes can be functionalized with, for example, sulfonic acid groups.

The invention provides several advantages. For example, the new methods and devices enable the practitioner or user to remove retroviruses and other viruses from blood, plasma, and commercial biological products without substantial removal or inactivation of proteins and other sample components, as evidenced by a minimal effect on the clotting time of plasma sanitized by the new methods. The new methods are highly effective and rapid, having been shown to result in the capture of at least 99.999% of the virus particles in a 100 ml sample (initially containing $1 \times 10^5$ particles per ml of plasma) in less than one hour, using a 2 cm long membrane. Additionally, the high capacity and flow rates discovered for these membranes are conducive to scale-up. Large volumes of culture medium containing recombinant retrovirus can be processed in a reasonably short period of time at high flow rates through hollow fiber cartridges containing diethylamino (DEA) membranes. Still larger volumes can be sanitized by using cartridges that include a plurality of hollow fibers in parallel or in series. The new methods can be adapted for use in existing hollow fiber systems.

The new methods can also be suitable for capturing and concentrating viruses, e.g., for use in gene therapy, since active viruses can, surprisingly, be eluted from the membranes after removal from a natural source or a growth medium. The virus preparations are ready for use after a simple desalting step that elutes the virus into a desired buffer or culture medium.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Membranes for Virus Capture

Figure 1:
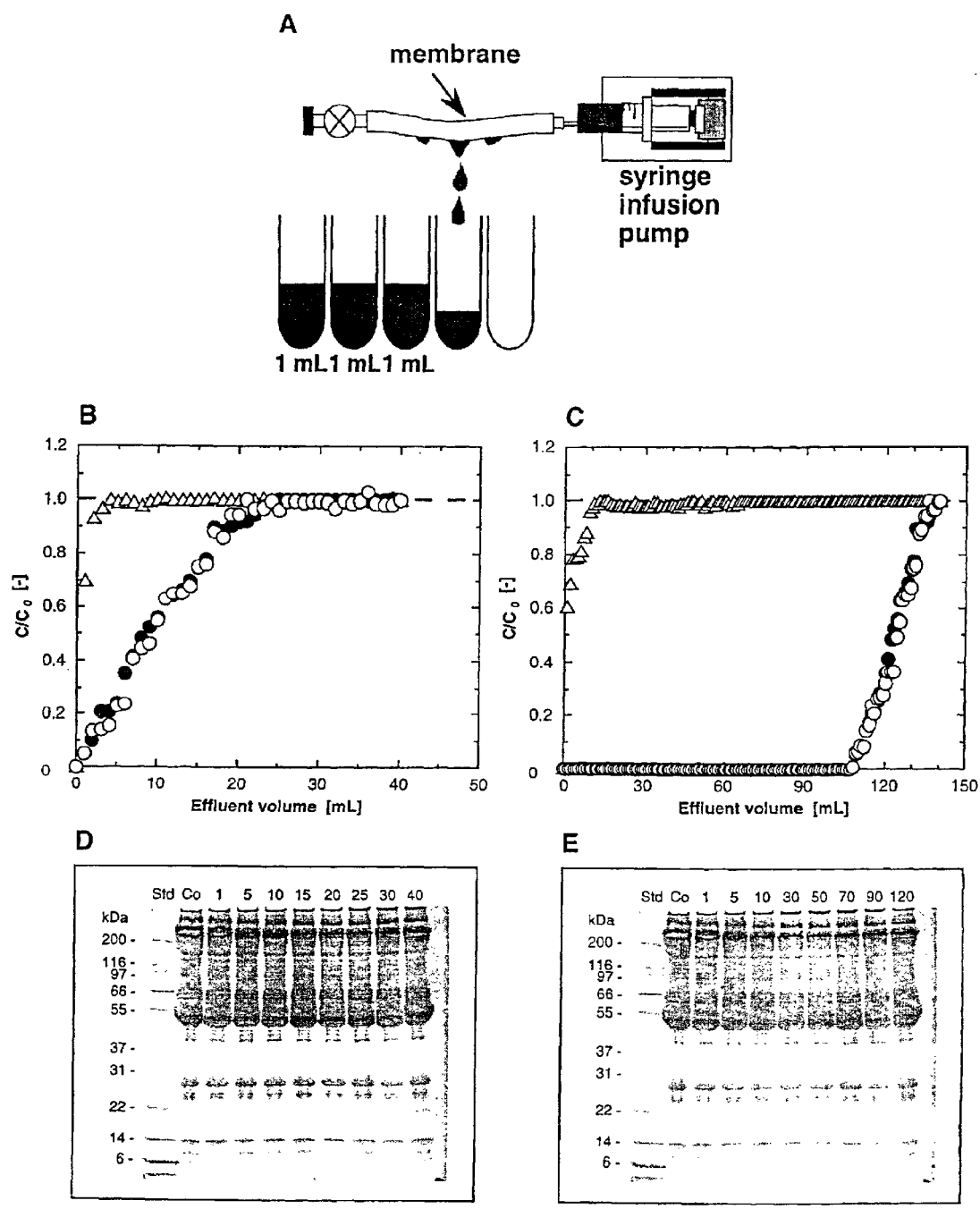
FIG. 1A is a diagram of an apparatus used for flowing recombinant retrovirus stock through a 2-cm long membrane.
FIGS. 1B–E are breakthrough curves of a glycidyl methacrylate (GMA) membrane (1B) and diethylamino (DEA) membrane (1C), with corresponding SDS-PAGE analysis of proteins in the collected effluents (1D and 1E, respectively).

In general, the membranes of the invention include a porous polymeric material (e.g., polyethylene, polypropylene, polysulfones, or polyether urethanes, or copolymers such as copolymers of polyethylene and polypropylene, or copolymers of polyethylene and polytetrafluoroethylene, in various sizes and shapes such as films, sheets, fibers, tubes, nonwoven fabrics, hollow fibers, and other configurations that such polymers can be fabricated into) with polymeric "brushes" attached to its surface. The porous polymeric material is functionalized, for example, by forming free radicals on its surface and reacting it with a vinyl monomer such as glycidyl methacrylate (GMA), 2-hydroxyethyl methacrylate (HEMA), or vinyl monomers having tertiary or quaternary amine functional groups. In some cases, the mass added in the functionalization process can exceed the mass of the original material (e.g., by about 2-, 3-, 5-, or even 10-fold); the ratio of mass added to original mass is referred to as the degree of grafting (dg).

Various techniques are known for free radical formation, including irradiation (e.g., γ-irradiation), UV treatment, plasma treatment, or exposure to chemical initiators. Radiation-induced graft polymerization (RIGP) methods, for example, are well known (see, e.g., Lee et al., Chem. Mater., 8:2618–2621, 1996 or Lee et al., Chem. Mater., 11:3091–3095, 1999) and are suitable for achieving a relatively high brush density on the surface of the porous polymeric material. RIGP methods include (1) irradiation of a backbone polymer (e.g., polyethylene) in the presence of a monomer, (2) irradiation of a backbone polymer in vacuo or under a nitrogen atmosphere, followed by grafting of monomer by trapped radicals, and (3) irradiation of a backbone polymer under an oxygen atmosphere, followed by grafting of monomer by polymeric peroxides. In general, as explained in Lee et al., 1999 (supra), the brush density (i.e., the number of side chains per unit of backbone polymer surface area) will depend on the length and intensity of irradiation: longer and/or more intense irradiation affords greater brush density. Side chain length will depend on the amount of monomer supplied as well as the length and intensity of irradiation of the backbone polymer. The more monomer supplied, the longer the chains will be at a given brush density. Where the monomer supply is constant but the brush density is increased (i.e., by longer and/or more intense irradiation), the brush length will be shorter.

A polyethylene film can, for example, be irradiated with an electron beam and subsequently reacted with a solution of glycidyl metharylate ($CH_2$=$CCH_3COOCH_2CHOCH_2$, GMA), resulting in graft-polymerization of the GMA onto the film, as described in Lee et al., J. Membrane Science, 81:295–305 (1993). GMA and other epoxy-containing monomers allow access to a wide variety of other functional groups via ring-opening reactions. Thus, for example, polymer brushes grafted on the porous trunk polymer material can be further modified to produce various functional groups that impart novel properties and functional capabilities. For example, the epoxy groups of the poly-GMA brushes react with amines such as diethylamine ($NH(CH_2CH_3)_2$) to form amino (e.g., diethylamino, DEA) groups. Primary or tertiary amines, or other reagents can similarly be used. Those of ordinary skill in the art would appreciate that any reagents that react with epoxides can be used in place of diethylamine in the preparation of the membranes. As a matter of routine experimentation, membranes made in this manner can be tested in the methods described below to identify those that are useful in capturing viruses with minimal removal of desired proteins.

The size of the membrane is ideally selected according to the requirements of the material to be purified. Larger or longer membranes can be used where greater capacity for pathogen removal or more rapid flow rates are desired. Optionally, a plurality of membranes (e.g., two, five, ten, fifty, 100, 500, 1000, or more) can be used in parallel or series in a hollow fiber or plate device. Such devices, using traditional ion-exchange or size exclusion membranes, are known in the art, and can be adapted to include the membranes of the invention (e.g., by replacement of the membranes).

Methods of Using the Membranes

The new methods of virus capture can be used in a variety of contexts.

Virus Removal from Blood and Other Biological Products

The new membranes can be used to eradicate viruses from plasma, and from commercial products such as recombinant protein preparations. In general, the liquids to be sanitized can be passed directly through the membranes to remove any viruses that may be present. Liquids containing cells (e.g., human blood) or other large particles typically require pre-treatment to separate the cells from the liquid prior to passing the liquid through the membrane, particularly if the cells or large particles are to be recombined with the sanitized liquid. Gases or vapors can also be passed through the new membranes, for example, to remove air-borne viruses.

Parameters such as sample temperature, pH, and salt concentration can be varied by the practitioner to accommodate a given material. Although the membranes can be operative at various temperatures (e.g., from the freezing point of the material up to its boiling point) for example, a given membrane will likely function best within a narrower range of conditions. For example, one membrane might be most active in the range of 4° C. to 20° C. Such information is readily available via routine experimentation. Additionally, the nature of the material to be sanitized may place restrictions on the conditions to be used in the process. For example, plasma containing relatively fragile proteins (e.g., clotting factors, the activity of which it would be desirable to maintain) should, where possible, be passed through the membranes at a temperature, pH, and salt concentration that is compatible with the maintenance of protein function. The practitioner would generally know which proteins' activities are to be maintained, and he or she can choose suitable conditions.

The rate at which the material is passed through the membrane can also have some bearing on the effectiveness of the method. Materials passed too quickly through the membrane may retain an unacceptably high level of pathogen, while those passed too slowly restrict the volume of material sanitized per unit of time.

Figure 4:
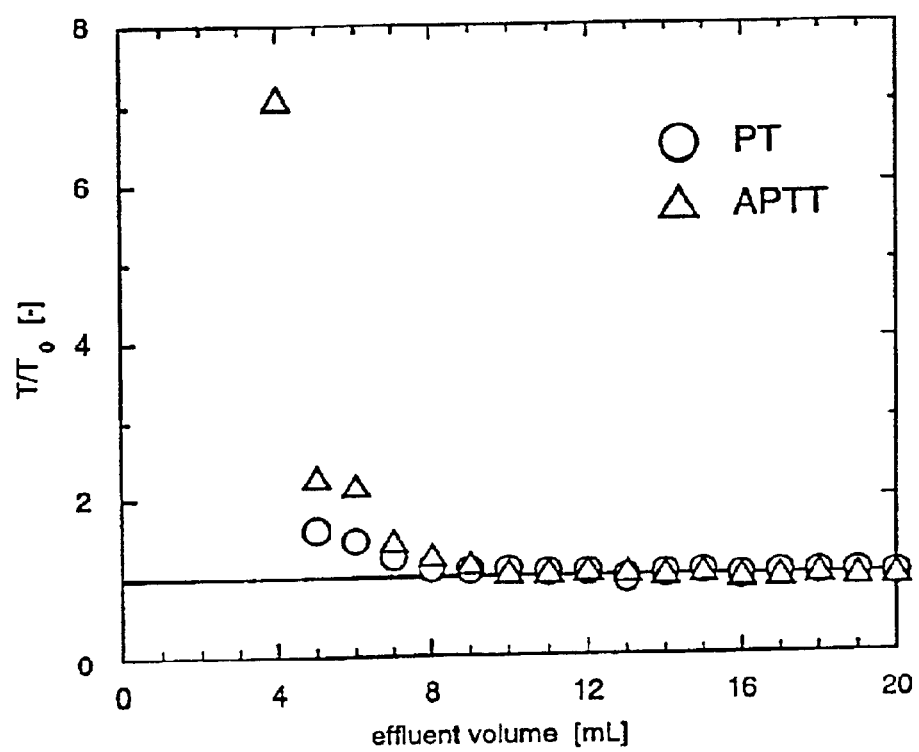
FIG. 4 is a plot of the ratio of clotting time after sanitization to clotting time prior to sanitization, as a function of volume of sample passed.

As noted above, retroviruses and other viruses can be removed from protein-containing materials such as blood, plasma, and commercial biological products (e.g., recombinant protein preparations) without substantial removal or inactivation of proteins. For example, prothrombin time (PT) and activated partial thromboplastin time (APTP), recognized in the field as useful indicators of the status of biologically important plasma enzymes, were measured for aliquots of a plasma sample sanitized via the methods described herein. The first few fractions of plasma passed through the membrane had increased PT and APTP values. Surprisingly, however, the PT and APTP values of all subsequent fractions were near normal, as shown by a $T/T_o$ ratio of 1 in FIG. 4 (($\Delta$) prothrombin time, ($\circ$) activated partial thromboplastin time). These results demonstrate that the new methods provide an effective, scalable process for capturing and removing viruses from protein-containing products such as human plasma without compromising the proteins therein.

The experiments described below demonstrate that viruses bound to the membranes in the course of carrying out the new sanitation methods can be eluted off from the membrane (e.g., with a salt solution). Hence, filtration devices including the new membranes can be reused, for example, after sterilization (e.g., by chemical or radiation treatment). Nonetheless, for certain applications, it is contemplated that the membranes or the entire devices would be disposed of after just one or a few uses.

Concentration and Purification of Viruses for Gene Therapy

The new membranes are also useful for the capture/purification and concentration of viruses used for gene therapy. For example, model recombinant retroviruses encoding the *E. coli* lacZ gene, can be captured by DEA membranes. In an actual example, virus-containing medium, harvested from a virus producer cell line in standard tissue culture medium containing 10% serum, was forced through a piece of either GMA membrane or DEA membrane at 4° C. using a syringe, as illustrated in FIG. 1A. With reference to FIGS. 1B and 1C, the collected effluents were quantitatively analyzed for: (1) total serum protein ($\Delta$), (2) bioactive lacZ retrovirus ($\bullet$), and (3) retrovirus p30 capsid protein ($\circ$). The value (C) of each fraction was normalized to the respective original concentration ($C_0$) in the starting virus stock. As shown in FIGS. 1B and 1C, the breakthrough point ($C/C_0=0.5$) for total protein occurred in approximately the first 0.5 ml for both types of membranes indicating that adsorption of serum proteins was minimal. When analyzed by SDS-PAGE, the full complement of serum proteins was present in all fractions (FIGS. 1D and 1E), suggesting that the adsorption of specific serum proteins was also minimal. In contrast, the breakthrough points for bioactive recombinant retrovirus, as well as p30 capsid protein, were dramatically different. For the GMA membrane, the breakthrough point occurred at 10 ml, whereas for the DEA membrane, the breakthrough point was 120 ml. The presence of tertiary amino functional groups on the DEA membrane resulted in a 12-fold increase in the capacity for capturing viruses. A small, 2-cm long piece of DEA membrane removed the approximately $10^7$ retroviral particles present in 100 ml of a 100 CFU/ml culture (FIG. 1C) (i.e., at least a 99.99999% reduction in viral titer).

Figure 2:
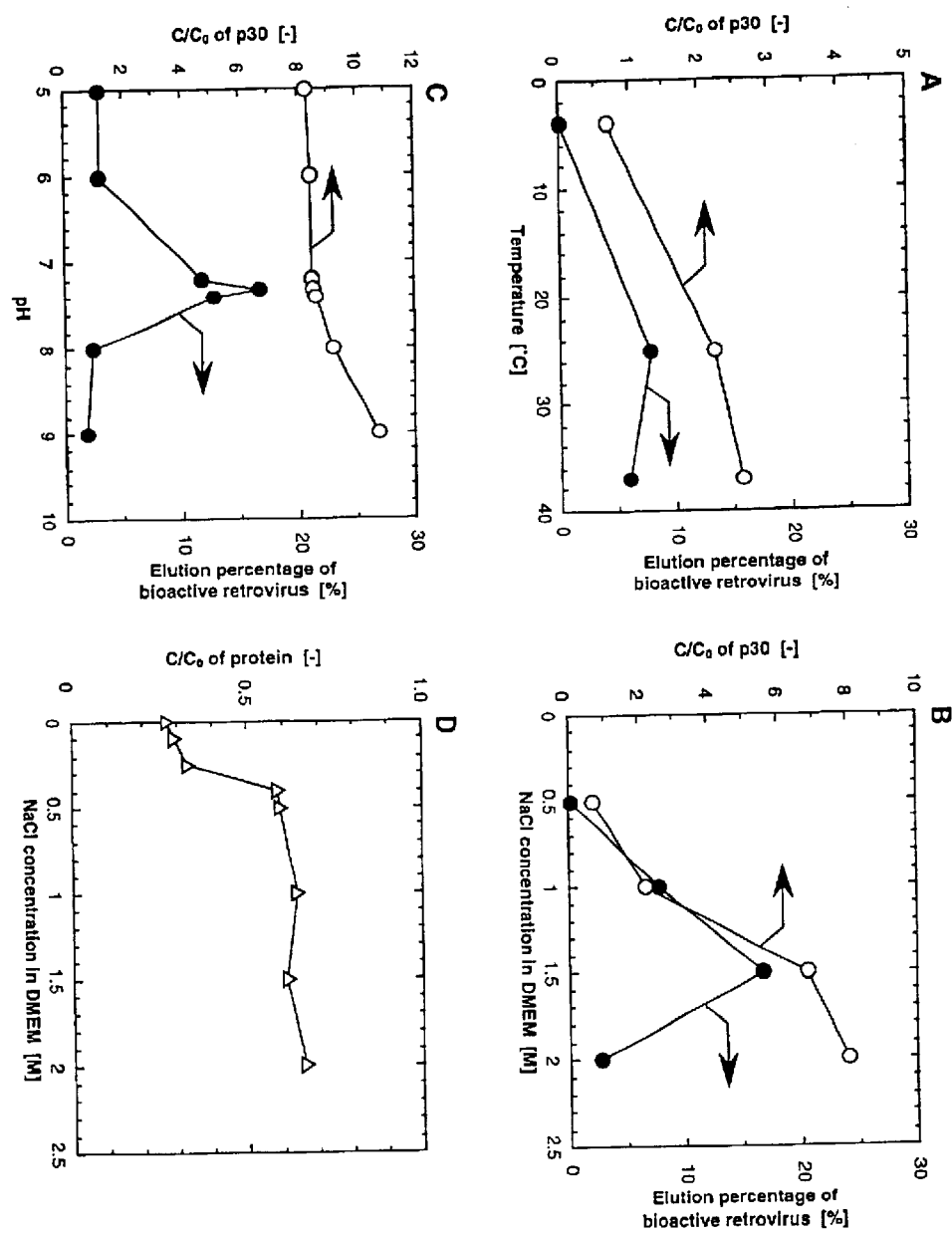
FIGS. 2A–C are plots of quantity of virus eluted with: (A) 1.0 M NaCl in DMEM at various temperatures; (B) various NaCl concentrations in DMEM at room temperature; and (C) 1.5 M NaCl in DMEM at various pHs at room temperature.
FIG. 2D is a plot of the quantity of protein eluted from the membrane at various NaCl concentrations in DMEM at room temperature.

With reference to FIGS. 2A–C, where ($\circ$) represents p30 capsid protein level and ($\bullet$) represents retrovirus titer, it was found that a high concentration of NaCl can be used to elute viruses captured by the DEA membrane and, surprisingly, that the viruses so eluted retained their bioactivity. To further optimize elution and preservation of activity, the influence of temperature, salt concentration and pH on elution was assessed. Elution with 1.0 M NaCl in DMEM at various temperatures showed that, although more particles were eluted at the higher temperature, their activity decreased above 25° C. (FIG. 2A), consistent with the relatively short half-life of retroviruses at ambient temperatures. Likewise, increasing concentrations of NaCl at room temperature also improved particle elution, but activity declined above 1.5 M (FIG. 2B). Virus activity was also found to be sensitive to the pH of the eluent (i.e., 1.5 M NaCl in DMEM). Particle elution increased as pH was increased, but optimal virus activity was preserved only within a narrow range of pH (7.2 to 7.4) (FIG. 2C).

Protein levels were also measured after elution with various concentrations of NaCl in DMEM. As shown in FIG. 2D, protein elution ($\Delta$) leveled off at 0.5 M NaCl indicating that these relatively low salt conditions can be used to selectively elute bound serum proteins with minimal removal of bound viruses.

Figure 3:
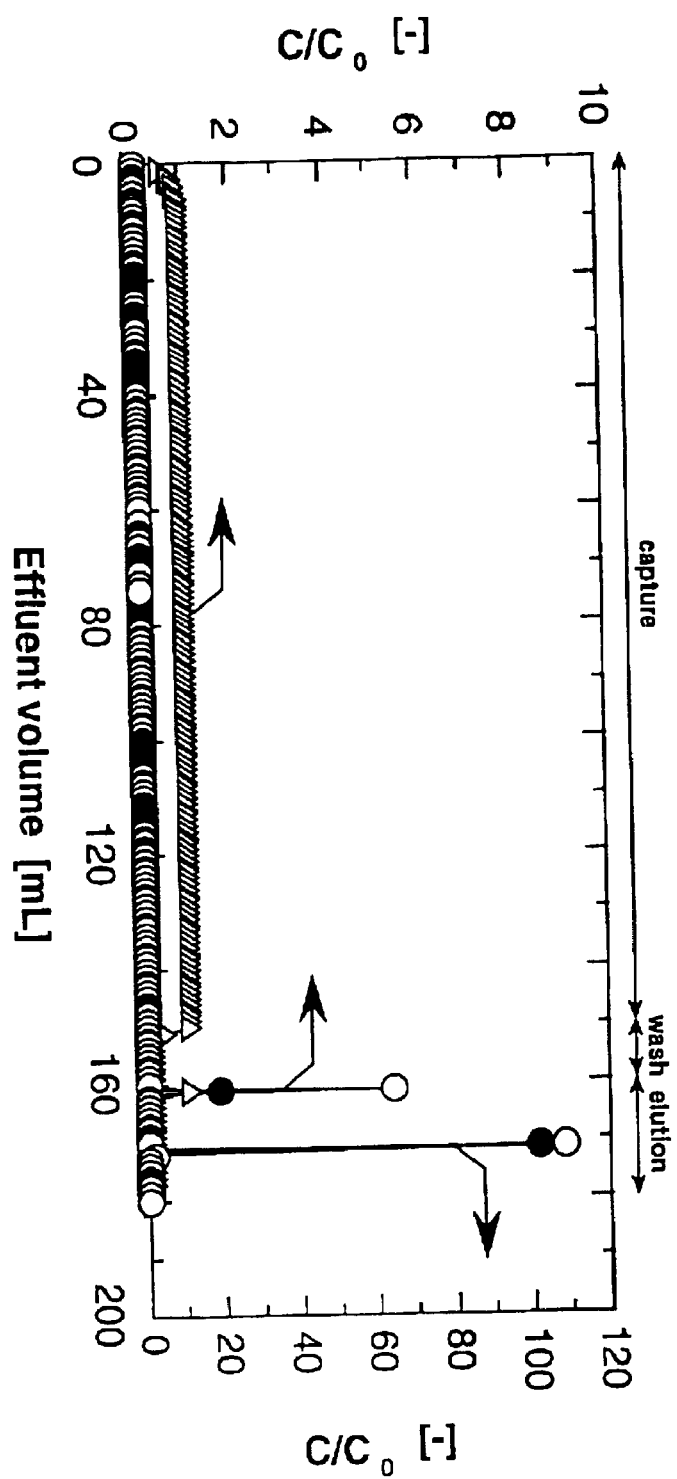
FIG. 3 is a plot of protein level, p30 capsid protein level, and retrovirus titer in a retrovirus capture/elution experiment; the titer of starting retrovirus stock solution was $1.0 \times 10^5$ CFU/ml.

As a test of the potential of these membranes to simultaneously capture, concentrate, and purify viruses, 150 ml of a lacZ virus stock was passed through 2 cm of a DEA membrane. The membrane was washed with 0.5 M NaCl in DMEM to remove bound serum proteins and then the virus was eluted with 1.5 M NaCl in DMEM (FIG. 3; ($\circ$) represents p30 capsid protein level and ($\bullet$) represents retrovirus titer). Each sample was quantitatively assayed for levels of serum protein, p30 capsid protein, and bioactive virus. Most serum protein was found to be eluted in the 0.5 M NaCl wash, and most retroviruses were eluted in the 1.5 M NaCl wash. As shown in Table 1, the retrovirus eluted in the 0.5 M NaCl wash had only 1% of the total activity of the starting stock and was concentrated 1.6-fold with only a 1.9-fold increase in purity. In contrast, the retrovirus eluted in the 1.5 M NaCl wash retained 67% of the total activity of the starting stock and was concentrated 100-fold with a 688-fold increase in purity compared to the starting stock.

TABLE 1

| | Retrovirus (CFU/ml) | Total retrovirus (CFU) | Protein (mg/ml) | Total protein (mg) | Specific activity (CFU/mg) |
|---|---|---|---|---|---|
| Stock | $1.0 \times 10^5$ | $1.5 \times 10^7$ | 12.5 | 1875 | $8.0 \times 10^3$ |
| Low salt wash, 1st ml eluted | $1.6 \times 10^5$ | $1.6 \times 10^5$ | 10.8 | 10.8 | $1.5 \times 10^4$ |
| High salt elution, 1st ml eluted | $1.1 \times 10^7$ | $1.1 \times 10^7$ | 2.0 | 2.0 | $5.5 \times 10^6$ |

Virus Production in New Bioreactors

DEA membranes can also be used as part of a continuous flow loop in which cells in a bioreactor (e.g., at 37° C.) produce viruses that are then captured by a DEA membrane (maintained at 4° C. where virus decay is negligible). In addition to being concentrated and purified after elution, the resulting virus preparation would have a higher fraction of active virus particles because the DEA membrane would have captured and stored the newly formed particles at 4° C., thus preventing their decay. With minimal decay, production times in this type of bioreactor design could be extended well beyond 24 hours to produce preparations with considerably more virus particles and significantly increased gene transfer potency.

The new bioreactors can be prepared, for example, according to the design of existing, commercially available bioreactors such as those sold by Cellco, Inc. (Germantown, Md.) or Hereaus (South Plainfield, N.J.). The hollow fibers of one of these commercial bioreactors can be replaced by hollow fibers of the invention to produce a new bioreactor. For example, the new bioreactor can include hundreds or thousands of hollow fibers of the invention, each a few centimeters (e.g., 2 cm) long and 1–4 mm in diameter. The new bioreactors can be further scaled up for commercial production or treatment of large volumes of pooled plasma.

Anti-Viral Therapies

The new membranes can also be used in an adjunctive therapy method. There are a large number of virus particles circulating in the blood of patients suffering from blood-borne viral infections such as hepatitis or HIV. Blood can be drawn from such a patient, the red and white blood cells from the patient's blood can be sequestered using a plasma separator (available, e.g., from Spectrum Labs, Inc., Laguna, Calif.), the plasma flow-through can be filtered according to the methods of the present invention, and the filtered plasma can be recombined with the red and white cells and reintroduced into the patient. This method will greatly reduce the patient's viral load, and can be continuous or can be repeated, e.g., daily, weekly, or monthly, as required.

Standard, commercially available filtration devices (e.g., hollow fiber devices, upstream prefilters, in-line filters, syringe filters) can be retrofitted with the new membranes for use in the filtration step, or new devices can be made having structures similar to or different from those of the commercially available devices. In general, such devices will include the new membranes together with any tubing, connectors, housings, and other components necessary to direct the material to be sanitized to and from the membrane. Other features can be included according to the desires of the manufacturer and end user. Alternatively or additionally, devices including the new membranes can be used in conjunction with commercially available devices (e.g., downstream from a prefilter such as those sold by Cuno, Inc., Meriden, Conn., or a size-exclusion device such as those sold by Pall Corp., East Hills, N.Y.). The new methods can be used in the manner and under the conditions suitable for use of existing filtration devices, as would be apparent to one of ordinary skill in the art.

Such treatment can also be used, for example, together with antiviral drugs. The method can be combined with any antiviral or antibiotic treatment, including multi-drug cocktails, anti-hepatitis drugs such as γ-interferon, and existing adjunct therapies.

EXAMPLE

The invention will be further described in the following example, which does not limit the scope of the invention described in the claims.

Preparation of Hollow-Fiber Membranes

A microporous polyethylene hollow-fiber membrane (inner diameter 1.9 mm, outer diameter 3.2 mm, porosity 70%, average pore size 340 nm) supplied by Asahi Chemical Industry Co., Ltd., Japan, was used as a trunk polymer. Glycidyl methacrylate ($CH_2=CCH_3COOCH_2CHOCH_2$; GMA), an epoxy-group containing vinyl monomer, was graft-polymerized onto the microporous polyethylene membrane by electron-beam-induced graft polymerization (Lee et al., 1993, supra). The amount of GMA grafted was defined as the degree of grafting (DG):

$$DG(\%)=[(\text{weight gained})/(\text{weight of trunk polymer})]\times 100$$

Polymer grafting of the GMA membrane was found to be about 200%, with an average side chain length of about 4700 GMA molecules and approximately $10^{18}$ side chains per gram of polyethylene. The GMA membranes were further reacted with diethylamine to convert the epoxy groups to diethylamino (DEA) groups. The resulting DEA membrane had a molar conversion of epoxy groups to diethylamino groups equal to 97%. All GMA and DEA membranes were sterilized and washed with 70% ethanol and double distilled water before use.

Cell Culture

NIH 3T3 cells and a Ψ-CRIP packaging cell line producing the amphotropic lacZ retrovirus were cultured in Dulbecco's modified Eagle medium (DMEM) (Gibco BRL, Gaithersburg, Md.) with 10% bovine calf serum (HyClone Labs, Inc., Logan, Utah) containing 100 U of penicillin and 100 μg of streptomycin per ml, as decribed in Morgan et al., J. Virol., 69:6994–7000 (1995). LacZ retrovirus-containing medium was harvested from confluent cultures of the packaging cell line, filtered through 0.45 μm syringe filters (Gelman Sciences, Ann Arbor, Mich.), frozen on pulverized dry ice, and stored at −85° C. for later use.

Capture and Elution of Recombinant Retrovirus

Membrane cylinders (GMA or DEA), 2-cm long, were positioned in a dead-end configuration to a syringe infusion pump (FIG. 1A). To condition the membranes, two milliliters of serum-free DMEM were permeated through the membranes. Next, retrovirus stock solution (15 or 150 ml) was flowed through the membranes at a constant flow rate (0.5 or 1 ml/min). Serum-free DMEM (5 ml) was flowed through to wash the membranes. Captured retroviruses were eluted by flow of a serum-free DMEM solution with additional salt concentration and pH as specified in FIG. 1A. During each of the steps, 1 ml samples of effluent were collected, frozen, and stored at −85° C. for later analysis. Serum protein concentration was determined using a BSA Protein Assay Kit (Pierce Chemical Company, Rockford, Ill.).

SDS-PAGE

Samples were mixed with an equal volume of 2×SDS sample buffer (126 mM Tris-HCl, 20% glycerol, 4% sodium dodecyl sulfate ("SDS"), 0.005% bromophenol blue (pH 6.8), boiled at 100° C. for 5 minutes, loaded onto a gradient (10–20%) Tris-glycine polyacrylamide gel (Novex, San Diego, Calif.), and resolved with 25 mA/gel in a Xcell II Mini Cell system (Novex) containing SDS running buffer (25 mM Tris base, 192 mM glycine, 0.1% SDS, pH 8.3). Gels were stained with Gelcode Blue Stain Reagent (Pierce) for 1 hour at room temperature followed by extensive washes in distilled water.

Diluted Titer Assay

Ten-fold serial dilutions of samples were adjusted to 8 μg/ml of Polybrene™ (1,5-dimethyl-1,5-diazaundecamethylene polymetho-bromide) (Sigma Chemical Co., St. Louis, Mo.). Two milliliters of these dilutions were used to infect NIH 3T3 cells that had been seeded at 60,000 cells/well in a 6-well plate the previous day. At 48 hours after the infection, the cells were fixed and stained for lacZ activity with X-gal (5-bromo-4-chloro-3-indolyl-D-galactopyranoside) (Boehringer Mannheim Corporation, Indianapolis, Ind.). Colonies of lacZ+ cells, which were typically clusters of two, four, or eight blue cells were counted and are reported in the above description as lacZ+ colony forming unit (CFU) per milliliter (Morgan et al., 1995, supra).

Clotting Assays

Aliquots were collected as plasma passed through the membrane. Each aliquot was assayed to measure prothrombin time (PT) and activated partial thromboplastin time (APTP) using commercially available PT and APTP assay kits (Sigma, St. Louis, Mo.), respectively. The data obtained for the first 20 ml are plotted in FIG. 4: the first few fractions of plasma passed through the membrane had increased PT (Δ) and APTP (○) values. The PT and APTP values of all subsequent fractions were near normal ($T/T_o \approx 1$).

Retrovirus p30 Capsid Protein ELISA

The concentration of p30 capsid protein was determined by ELISA (Rigg et al., Virology, 218:290–295, 1996).

ELISA plates (Fisher Scientific, Agawan, Mass.) were coated with 10 µg/ml mouse anti-p30 antibody (CRL-1912 hybridoma cell line) (ATCC, Rockville, Md.) (100 µl/well) in PBS overnight at 4° C. The next day, the antibody solution was removed and BLOTTO™ Blocker in TBS (Pierce, Rockford, Ill.) was added (150 µl/well) for 2 hours at 37° C. Samples were denatured for 5 minutes at >90° C., added to the ELISA plate (100 µl/well) and incubated for 1 hour at 37° C. The plate was washed and a polyclonal goat anti-p30 antibody (78S221)(Quality Biotech, Camden, N.J.) diluted 1:1000 in BLOTTO™ Blocker in TBS was added and incubated for 1 h at 37° C. The plate was washed and an HRP-conjugated rabbit anti-goat IgG polyclonal antibody (Calbiochem-Novabiochem International, San Diego, Calif.) diluted 1:1000 was added (100 µl/well) and incubated for 1 hour at 37° C. An o-phenylenediamine ("OPD") pill (Sigma) (10 mg) was dissolved in substrate buffer (25 ml) at room temperature with 10 µl of 30% $H_2O_2$ added. The OPD solution was added (100 µl/well) and after 5 minutes the reaction was stopped with 8N $H_2SO_4$ (50 µl/well). Optical density at 490 nm ("OD490") was measured and nonspecific background at 650 nm subtracted. Data corresponding to each point in FIGS. 1B, 1C, 2D, and 3 are the average over at least three iterations of the experiment.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for removing a virus from a liquid sample, the method comprising:
   obtaining a membrane engrafted with polymeric side chains, each side chain having one or more positively charged functional groups that interact with viruses, the polymeric side chains each having one functional group per repeat unit, each functional group consisting of a single secondary, tertiary, or guaternary amine, and having a single positive charge at physiological pH, wherein the membrane has a nominal pore sizebetween 20 nm and 1000 nm; and
   passing the sample through the membrane to remove viruses from the sample.

2. The method of claim 1, wherein the membrane has a nominal pore size between 200 nm and 500 nm.

3. The method of claim 1, wherein the membrane comprises polypropylene and the polymeric side chains comprise diethylaminated poly(glycidyl methacrylate).

4. The method of claim 1, wherein the polymeric side chains have an average length between 50 nm and 2000 nm.

5. The method of claim 1, wherein the polymeric side chains have an average length between 500 nm and 1000 nm.

6. The method of claim 1, wherein between 1.0e16 and 1.0e20 of the side chains are engrafted per square meter of the membrane's surface area.

7. The method of claim 1, wherein between 1.0e17 and 1.0e18 of the side chains are engrafted per square meter of the membrane's surface area.

8. The method of claim 1, wherein the membrane has a degree of grafting between 50% and 500%.

9. The method of claim 1, wherein the membrane has a degree of grafting between 150% and 300%.

10. The method of claim 1, wherein the method is effective to remove at least 99.999% of virus particles from the sample.

11. The method of claim 1, wherein the method is effective to remove at least 99.99999% of virus particles from the sample.

12. The method of claim 1, wherein the virus is a retrovirus.

13. The method of claim 1, wherein the sample comprises a protein, and wherein less than 10% of the protein is removed from the sample in said passing step.

14. The method of claim 13, wherein less than 2% of the protein is removed from the sample.

15. The method of claim 13, wherein the sample is a plasma sample, and the method results in less than a five-fold increase in the plasma sample's clotting time.

16. The method of claim 1, wherein the sample flows through the membrane at a rate of 1 to 1000 ml/min per square centimeter of membrane.

17. The method of claim 1, wherein the sample flows through the membrane at a rate of 20 to 200 ml/min per square centimeter of membrane.

18. The method of claim 1, further comprising eluting the virus from the membrane with an eluent solution to obtain a suspension of substantially purified virus in the eluent solution.

19. The method of claim 18, wherein the eluent solution comprises sodium chloride.

20. The method of claim 18, wherein the purified virus is bioactive.

21. The method of claim 18, wherein the purified virus is concentrated more than 100-fold relative to the sample.

22. The method of claim 1, wherein at least 97% of the polymeric repeats are covalently linked to a positively charged functional group.

23. The method of claim 1, wherein the membrane was engrafted using electron beam irradiation and incubation with a precursor of the polymeric side chain.

24. The method of claim 23, wherein the precursor of the polymeric side chain is glycidyl methacrylate.

25. The method of claim 1, wherein the method is effective to remove at least 99.99999% of virus particles from the sample when the sample comprises approximately $10^7$ retroviral particles in 100 ml and the membrane is a hollow cylinder, about 2 cm in length and about 1–4 mm in diameter.

26. A method for removing a virus from a liquid sample, the method comprising
   obtaining a membrane engrafled with polymeric side chains having one or more positively charged functional groups that interact with viruses, wherein at least 97% of the polymeric repeats are covalently linked to a positively charged functional group, the membrane has a nominal pore size between 20 nm and 1000 nm; and
   passing the sample through the membrane to remove viruses from the sample.

27. The method of claim 26, wherein the positively charged functional group is an amino group.

28. The method of claim 26, wherein the positively charged functional group is a diethylamino group.

* * * * *